United States Patent
Negrisoli et al.

(10) Patent No.: US 11,420,943 B2
(45) Date of Patent: Aug. 23, 2022

(54) PEPTIDE DERIVATIVES AND THERAPEUTIC ACTIVITY THEREOF

(71) Applicant: FLAMMA S.P.A., Chignolo d'Isola (IT)

(72) Inventors: GianPaolo Negrisoli, Chignolo d'Isola (IT); Stefania Gagliardi, Chignolo d'Isola (IT); Almin Silnovic, Chignolo d'Isola (IT); Clelia Dallanoce, Milan (IT); Marco De Amici, Pavia (IT); Renato Canevotti, Chignolo d'Isola (IT)

(73) Assignee: FLAMMA S.P.A., Chignolo d'Isola (IT)

( * ) Notice: Subject to any disclaimer, the term of this patent is extended or adjusted under 35 U.S.C. 154(b) by 0 days.

(21) Appl. No.: 16/958,336

(22) PCT Filed: Dec. 19, 2018

(86) PCT No.: PCT/IB2018/060332
§ 371 (c)(1),
(2) Date: Jun. 26, 2020

(87) PCT Pub. No.: WO2019/130164
PCT Pub. Date: Jul. 4, 2019

(65) Prior Publication Data
US 2020/0361875 A1 Nov. 19, 2020

(30) Foreign Application Priority Data

Dec. 27, 2017 (IT) .......................... 102017000149628

(51) Int. Cl.
*C07D 233/64* (2006.01)
(52) U.S. Cl.
CPC .................................. *C07D 233/64* (2013.01)
(58) Field of Classification Search
CPC .................................................. C07D 233/64
USPC ....................................................... 514/400
See application file for complete search history.

(56) References Cited

U.S. PATENT DOCUMENTS 8,623,900 B2 * 1/2014 Negrisoli ................ A61P 25/00
548/335.5

FOREIGN PATENT DOCUMENTS

| WO | 2008/001174 | 1/2008 |
| WO | WO-2008001174 A1 * | 1/2008 .............. A61P 27/12 |
| WO | 2011/080139 | 7/2011 |

OTHER PUBLICATIONS

Fink, Journal of Medicinal Chemistry (1995), 38(26), 5023-30.*
Moffitt, Biochemical and Biophysical Research Communications, (1978), 83(4), 1415-21.*
International Search Report and Written Opinion of the International Searching Authority, dated Feb. 19, 2019 in corresponding International Patent Application No. PCT/IB2018/060332.
Guiotto et al., "Carnosine and Carnosine-Related Antioxidants: A Review", Current Medicinal Chemisuy, 12: 2293-2315 (2005).
Vistoli et al., "Design, Synthesis, and Evaluation of Carnosine Derivatives as Selective and Efficient Sequestering Agents of Cytotoxic Reactive *Carbonyl* Species", Chem. Med. Chem., 4(6): 967-975 (2009).
Furfaro et al., "HNE-dependent molecular damage in diabetic nephropathy and its possible prevention by N-acetyl-cysteine and oxerutin", BioFactors, 24: 291-298 (2005).
Chiarpotto et al., "Role of 4-hydroxy-2,3-nonenal in the pathogenesis of fibrosis", BioFactors, 24: 229-236 (2005).
Aldini et al., "Carnosine is a quencher of 4-hydroxy-nonenal: through what mechanism of reaction?", Biochemical and Biophysical Research Communications, 298: 699-706 (2002).
Zarkovic, "4-Hydroxynonenal and neurodegenerative diseases", Molecular Aspects of Medicine, 24: 293-303 (2003).
Uchida, "4-Hydroxy-2-nonenal: a product and mediator of oxidative stress", Progress in Lipid Research, 42: 318-343 (2003).
Zarkovic, "4-Hydroxynonenal as a bioactive marker of pathophysiological processes", Molecular Aspects of Medicine, 24: 281-291 (2003)
Leonarduzzi et al., "4-Hydroxynonenal and cholesterol oxidation products in atherosclerosis", Mol. Nutr. Food Res., 49: 1044-1049 (2005).
Hipkiss, "Could Carnosine or Related Structures Suppress Alzheimer's Disease", Journal of Alzheimer's Disease, 11: 229-240 (2007).
Poli et al., "4-Hydroxynonenal in the Pathomechanisms of Oxidative Stress", IUBMB Life, 50: 315-321 (2000).
Uchida, "Role of Reactive Aldehyde in Cardiovascular Diseases", Free Radical Biology & Medicine, 28(12), 1685-1696 (2000).
Esterbauer et al., "Chemistry and Biochemistry of 4-Hydroxynonenal, Malonaldehyde and Related Aldehydes", Free Radical Biology & Medicine, 11:81-128 (1991).

* cited by examiner

*Primary Examiner* — Nizal S Chandrakumar
(74) *Attorney, Agent, or Firm* — Wenderoth, Lind & Ponack, L.L.P.

(57) ABSTRACT

Disclosed are peptide or pseudopeptide derivatives containing a nitrogenous heterocyclic residue with blocking activity against the by-products of lipid oxidative stress, and in particular of unsaturated aldehydes such as malondialdehyde and 4-hydroxy-trans-2-nonenal (HNE).

9 Claims, No Drawings

PEPTIDE DERIVATIVES AND THERAPEUTIC ACTIVITY THEREOF

The present invention relates to dipeptide or pseudodipeptide derivatives containing an aminoalkanoyl group disubstituted on at least one of the carbon atoms of the chain, with metabolic quenching activity towards carbonyl compounds.

PRIOR ART

The influence of oxidative damage on triggering various physiopathological processes, including aging, inflammatory disorders, diabetes, cardiovascular disease and neurodegenerative processes, has long been recognised. The main molecular mechanisms responsible for oxidative damage, such as structural damage to proteins, lipids and nucleic acids caused by radical reactive oxygen species, and an altered cell redox state, are also well known [Halliwell B, Gutteridge J M. Free Radicals in Biology and Medicine (2001) Oxford Science Publications, 3rd Ed.].

It has also been clarified that some products of lipid oxidation characterised by a keto/aldehyde function act as important cytotoxic oxidative mediators, inducing irreversible structural modifications of the biomolecules, leading to alteration of the cell functions [Uchida K. Free Radic. Biol. Med. 2000; 28:1685-96; Poli G. et al., IUBMB Life. 2000; 50:315-21].

The carbonyl compounds studied include the products of oxidation of polyunsaturated fatty acids, including alpha, beta-unsaturated aldehydes such as 4-hydroxy-trans-2-nonenal (HNE) and acrolein (ACR) [Esterbauer H. et al., Free Radic. Biol. Med. 1991; 11:81-128].

The participation of unsaturated aldehydes in various pathological processes with an oxidative basis has been demonstrated with the use of mono- and polyclonal antibodies [Uchida K. Prog. Lipid Res. 2003; 42:318-43]. In particular, adducts between HNE and acrolein with proteins have been identified in biopsy and autopsy tissue of patients suffering from diabetes, atherosclerosis, muscular dystrophy, rheumatoid arthritis, actinic elastosis, cerebral ischaemia and neurodegenerative diseases such as Alzheimer's disease and Parkinson's disease [Uchida K. Prog. Lipid Res. 2003; 42:318-43; Zarkovic N. Mol. Aspects Med. 2003; 24:281-91; Zarkovic N. Mol. Aspects Med. 2003; 24:293-303; M. Carini et al. in "Redox Proteomics: from Protein Modifications to Cellular Dysfunction and Diseases" (Ed. I. Dalle-Donne, A. Scaloni, and A. Butterfield); Wiley Inter-Science Books from John Wiley & Sons (2005)].

The role of HNE as a pathogenetic factor has been demonstrated at molecular level for various disorders such as fibrosis [Chiarpotto E. et al., Biofactors. 2005; 24 (1-4): 229-36], diabetic nephropathy [Furfaro A L. et al. Biofactors. 2005; 24 (1-4): 291-8.], atherosclerotic processes [Leonarduzzi G. et al., Mol Nutr Food Res. 2005 November; 49 (11):1044-9] and neurodegenerative disorders [Zarkovic K. Mol Aspects Med. 2003 August-October; 24 (4-5):293-303].

It is therefore evident that carbonyl products, especially reactive carbonyl compounds such as HNE, are important targets for the development of a new class of biologically active molecules with carbonyl-quenching activity.

This interest is clearly demonstrated by the considerable number of articles and patents describing compounds with carbonyl-quenching activity, especially dipeptide compounds correlatable with carnosine [Hipkisss A. R., J. Alzheimer's Dis. 2007, 11, 229-240; Guiotto A. et al. Curr. Med. Chem. 2005, 12, 2293-2315; Vistoli G. et al., Chem. Med. Chem. 2009, 4 (6), 967-975].

Peptide compounds which are structurally correlatable with carnosine and their carbonyl-quenching activity are also described, for example, in WO2008/001174, while some aminoalcohol derivatives are described in WO2011/080139.

DESCRIPTION OF THE INVENTION

The present invention relates to peptide or pseudopeptide derivatives containing a nitrogenous heterocyclic residue which have demonstrated an interesting activity of blocking the by-products of oxidative lipid stress, in particular those of unsaturated aldehydes such as malondialdehyde and 4-hydroxy-trans-2-nonenal (HNE), which are known for their contribution to the onset of a considerable number of chronic disorders such as neurodegenerative disorders, chronic inflammatory disorders, cardiovascular disease, and complications of diabetes and cataract. This novel series of compounds, studied as from the structure of the endogenous L-carnosine dipeptide present in some tissues of the human body, is characterised by the presence of a double substitution on one of the carbons of the beta-alanine chain and the presence of a hydroxymethyl group optionally substituted for the terminal carboxyl group of L-carnosine. The compounds have demonstrated a surprisingly greater activity of the dipeptide L-carnosine and the corresponding aminoalcohols in quenching model carbonyl compounds, and extremely high metabolic stability compared with that of L-carnosine or structurally correlated compounds. These characteristics make them suitable for therapeutic use in all disorders correlatable with the presence of reactive carbonyl compounds.

The invention also relates to said compounds for use in the treatment or prevention of said disorders.

The compounds forming the object of the invention have the general formula I

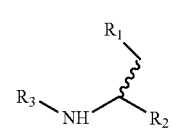

wherein:

$R_1$ is a 5-6 membered heterocyclic ring optionally fused to a benzene ring, containing one to three nitrogen atoms optionally bearing $C_1$-$C_3$ alkyl substituents;

$R_2$ is:

a $CH_2$—O—R group wherein R represents hydrogen, a straight or branched $C_1$-$C_{10}$ alkyl group or a $C_3$-$C_8$ cycloalkyl group, a straight or branched $C_1$-$C_8$ alkylcarbonyl group, a $C_3$-$C_8$ cycloalkylcarbonyl group; or R is an $Ar(CH_2)_pC(=O)$— group wherein Ar is an aryl selected from phenyl and naphthyl optionally substituted with one or two groups selected from the group of methyl, methoxy or ethyl, and p is zero or an integer between 1 and 3;

a $COOR_8$ group wherein $R_8$ represents hydrogen, a straight or branched $C_1$-$C_{10}$ alkyl group or a $C_3$-$C_8$ cycloalkyl group;

$R_3$ is a group of general formula II

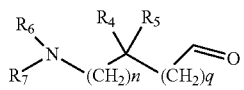

wherein n and q, independently of one another, are equal to zero or represent an integer between 1 and 4;

$R_6$ and $R_7$, which are the same or different, represent:

hydrogen;

a straight or branched $C_1$-$C_{20}$ alkylcarbonyl group or a $C_3$-$C_7$ cycloalkylcarbonyl group optionally containing one or more double bonds, or an $Ar(CH_2)_pC(=O)—$ group wherein Ar and n are as defined above;

a straight or branched $C_1$-$C_{10}$ alkoxycarbonyl group or a $C_3$-$C_7$ cycloalkoxycarbonyl group optionally containing one or more double bonds, or an $ArO(CH_2)_nC(=O)—$ group wherein Ar and n are as defined above;

one of $R_6$ and $R_7$ is an amino group and the other is hydrogen;

one of $R_6$ and $R_7$ is hydrogen and the other is a group of formula III

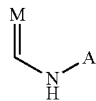

wherein M represents nitrogen, oxygen or sulphur and A represents hydrogen or an amino group, and the free valence of the carbon atom forms a bond with the nitrogen atom of the group of formula II;

$R_4$ and $R_5$, which are the same or different, represent:

a straight or branched $C_1$-$C_8$ alkyl group, preferably methyl;

a halogen, preferably fluorine;

can be joined to form, together with the carbon atom to which they are linked, a cycloaliphatic ring with 3 to 6 carbon atoms selected from cyclopropyl, cyclobutyl, cyclopentyl and cyclohexyl forming an $R_3$ group of general formula IV

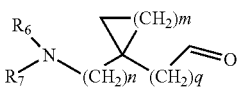

wherein m has a value ranging between 1 and 4;

$R_6$, $R_7$, n and q have the meanings described above.

In general formula I, wavy bond ⁓ indicates that the carbon atom substituted with NH and $R_2$ can have the R or S configuration.

In general formulas II and IV, the free valence of the carbon atom of the carbonyl group forms a bond with the nitrogen atom of formula I.

Examples of a 5-6 member heterocyclic ring comprise imidazole, pyrrole, pyrazole, triazole, indole, isoindole, indazole, benzoimidazole and benzotriazole.

In one embodiment of the invention:

$R_1$ is a heterocyclic ring selected from imidazole, pyrrole, pyrazole, triazole, indole, isoindole, indazole, benzoimidazole and benzotriazole, preferably imidazole or imidazole substituted at the nitrogen atom at the 1-position or at the 3-position with methyl, ethyl or propyl;

$R_2$ and $R_3$ are as defined above.

In another embodiment of the invention:

$R_1$ is imidazole optionally substituted at the nitrogen atom at the 1-position or at the 3-position with methyl, ethyl or propyl;

$R_2$ is $CH_2$—OH or a $COOR_8$ group wherein $R_8$ is selected from hydrogen, methyl and ethyl.

$R_3$ is a group of formula II wherein $R_4$ and $R_5$ are both methyl or halogen, $R_6$ and $R_7$ are both hydrogen, or one of $R_6$ and $R_7$ is hydrogen and the other is a straight or branched $C_1$-$C_{10}$ alkoxycarbonyl group or a $C_3$-$C_7$ cyclic group, and n and q are as defined above.

In another embodiment of the invention:

$R_1$ is imidazole optionally substituted at the nitrogen atom at the 1-position or at the 3-position with methyl, ethyl or propyl;

$R_2$ is $CH_2$—OH or a $COOR_8$ group wherein $R_8$ is selected from hydrogen, methyl and ethyl;

$R_3$ is a group of formula IV wherein $R_4$ and $R_5$ are joined to form, together with the carbon atom to which they are bonded, a cycloaliphatic ring with 3 to 6 carbon atoms selected from cyclopropyl, cyclobutyl, cyclopentyl and cyclohexyl, $R_6$ and $R_7$ are both hydrogen, or one of $R_6$ and $R_7$ is hydrogen and the other is a straight or branched $C_1$-$C_{10}$ alkoxycarbonyl group or a $C_3$-$C_7$ cyclic group, and m, n and q are as defined above.

In a preferred embodiment:

$R_1$ is imidazole optionally substituted at the nitrogen atom at the 1-position or at the 3-position with methyl;

$R_2$ is $CH_2$—OH or a $COOR_8$ group wherein $R_8$ is hydrogen;

$R_3$ is a group of formula II wherein $R_4$ and $R_5$ are both methyl or fluorine, $R_6$ and $R_7$ are both hydrogen, and n and q are as defined above.

In another preferred embodiment:

$R_1$ is imidazole optionally substituted at the nitrogen atom at the 1-position or at the 3-position with methyl;

$R_2$ is $CH_2$—OH or a $COOR_8$ group wherein $R_8$ is hydrogen.

$R_3$ is a group of formula IV wherein $R_4$ and $R_5$ are joined to form, together with the carbon atom to which they are bonded, a cycloaliphatic ring with 3 to 6 carbon atoms selected from cyclopropyl, cyclobutyl, cyclopentyl and cyclohexyl, $R_6$ and $R_7$ are both hydrogen, and m, n and q are as defined above.

Examples of compounds according to the invention are:

(S)-2-amino-N-(1-hydroxy-3-(1H-imidazol-4-yl)propan-2-yl)-2-methylpropanamide;

(S)-3-amino-N-(1-hydroxy-3-(1H-imidazol-4-yl)propan-2-yl)-2,2-dimethylpropanamide;

(S)-4-amino-N-(1-hydroxy-3-(1H-imidazol-4-yl)propan-2-yl)-2,2-dimethylbutanamide;

(S)-1-(aminomethyl-N-(1-hydroxy-3-(1H-imidazol-4-yl)propan-2-yl)cyclopropanecarboxamide;

(S)-1-(aminomethyl-N-(1-hydroxy-3-(1H-imidazol-4-yl)propan-2-yl)cyclobutanecarboxamide;

(S)-1-(aminomethyl-N-(1-hydroxy-3-(1H-imidazol-4-yl)propan-2-yl)cyclopentanecarboxamide;

(S)-1-(aminomethyl-N-(1-hydroxy-3-(1H-imidazol-4-yl)propan-2-yl)cyclohexanecarboxamide;

(S)-3-amino-N-(1-hydroxy-3-(1-methyl-1H-imidazol-5-yl)propan-2-yl)-2,2-dimethylpropanamide;

(S)-3-amino-N-(1-hydroxy-3-(1H-imidazol-4-yl)propan-2-yl)-3,3-dimethylpropanamide;
(S)-3-amino-2,2-difluoro-N-(1-hydroxy-3-(1H-imidazol-4-yl)propan-2-yl)-propanamide;
N-(2-amino-2-methylpropanoyl)-L-histidine;
N-(3-amino-2,2-dimethylpropanoyl)-L-histidine
N-(1-aminomethyl)-1-cyclopropylcarbonyl)-L-histidine;
N-(1-aminomethyl)-1-cyclclobutylcarbonyl)-L-histidine;
N-(1-aminomethyl)-1-cyclopentylcarbonyl)-L-histidine
N-(1-aminomethyl)-1-cyclohexylcarbonyl)-L-histidine;
N-(4-amino-2,2-dimethylbutanoyl)-L-histidine;
N-(3-amino-3,3-dimethylpropanoyl)-L-histidine;
N-(3-amino-2,2-dimethylpropanoyl)-L-histidine
N-(3-amino-2,2-difluoropropanoyl)-L-histidine.

example, crystallisation, chromatographic purification or any other technique required to obtain compounds with the required degree of purity.

By way of example, the compounds according to the invention can be prepared according to synthesis scheme 1. A suitable aminoester of formula VI wherein R is a $C_1$-$C_3$ alkyl is coupled with the corresponding protected amino acid of formula VII wherein $R_4$, $R_5$, n and q are as defined above, and $R'_6$ is a protecting group of the nitrogen atom according to one of the known methods, and the resulting protected dipeptide ester of formula VIII can subsequently be reduced to the corresponding alcohol IX and deprotected to obtain the corresponding aminoalcohol X. Alternatively, the protected dipeptide ester of formula VIII can be hydrolysed and deprotected to obtain the peptides of formula XI.

Synthesis scheme 1

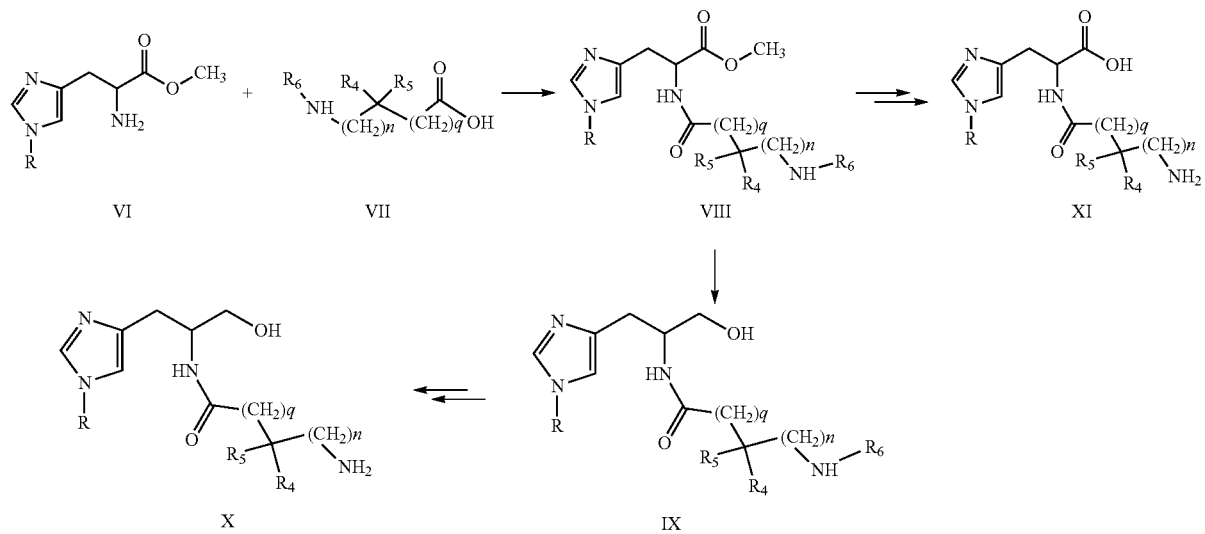

As at least one chiral centre is present in the compounds of formula I, all the optical isomers of the products in question and the mixtures thereof in any proportion, and all the possible diastereoisomers, taken individually or mixed together in any proportion, are deemed to constitute an integral part of the invention. All the pharmacologically acceptable salts of the products of formula I are also part of the invention.

The compounds according to the invention were synthesised by some of the well-known solid-phase or solution-phase peptide synthesis methods reported in the literature, for example in Houben-Weil "Synthesis of peptides and peptidomimetics" vol. E22 a-d or J. Jones "Amino acid and peptide synthesis". The amino acids used in the synthesis, if not available in an already protected form, were suitably functionalised with the necessary protecting groups using well-known methods, such as those reported in T. W. Greene, P. G. M. Wuts "Protective group in organic synthesis" or P. J. Kocienski "Protecting groups". The aminoalcohols used in the synthesis were prepared by reduction of derivatives of the corresponding amino acids using suitable metal or organometal hydrides in inert solvents, and similar procedures were used in the reduction of dipeptide to aminoacylaminoalcohol derivatives.

The end products obtained were purified, when necessary, by one of the methods known to the skilled person, using, for The pharmacological activity of the compounds according to the invention was determined in vitro by evaluating their carbonyl-quenching activity towards 4-hydroxy nonenal (HNE), which is known for its involvement in numerous disorders. Said activity was compared with that of L-carnosine, a compound known as a carbonyl quencher in vitro but having limited metabolic stability caused by serum carnosinase. The metabolic stability of a particularly interesting compound was also evaluated in human serum after 1 and 2 hours.

The results of the pharmacological tests clearly demonstrate that some of the compounds according to the invention possess carbonyl-quenching activity which is considerably greater than that of L-carnosine and significantly greater than that of other compounds that do not bear substituents on the alkyl chain, which are described above. For this purpose it is interesting to compare the compound 2-amino-N-(1-hydroxy-3-(1H-imidazol-4-yl)propan-2-yl)-2-methylpropanamide (FLM-04-OLO) forming the object of the present invention, which exhibits carbonyl-quenching activity 3.1 times greater than that of L-carnosine (see Table I), with that of the non-disubstituted derivative 3-amino-N-[(1S)-2-hydroxy-1-(1H-imidazol-5-yl-methyl)ethyl]propanamide reported in WO2011/080139, an activity whereof, 1.6 times greater than that of L-carnosine, is reported in the same test.

For the intended uses, the compounds of formula I are conveniently formulated in conventional pharmaceutical, cosmetic or nutritional compositions suitable for oral, parenteral, topical or transdermal administration, which constitute a further object of the invention. Examples of said compositions include capsules, tablets, syrups, injectable solutions or suspensions, ointments, suppositories, controlled-release forms and the like, and water-soluble granulates. Said forms, plus carriers and excipients used in pharmaceutical technology, could optionally also contain other active ingredients which have a complementary activity or are otherwise useful for the treatment/prevention of the disorders in question. The invention is illustrated in detail in the following examples.

General Example of Procedure 1

In an anhydrous medium, under argon, the acid of structure VII (1 equiv.) is dissolved in anhydrous $CH_3CN$ (5 mL/mmol), and the mixture is cooled to 0° C. HATU (1.05 equiv.) is added, and DIPEA (2 equiv.) is dripped in. The reaction mixture is left under magnetic stirring at 0° C. for 5 min, and a solution of compound VI (1 equiv.) and DIPEA (2 equiv.) in anhydrous $CH_3CN$ (5 mL/mmol) is then dripped in. The resulting mixture is left under stirring at room temperature for 2-4 hours. At the end of the reaction (TLC assay [DCM/MeOH 7:3]) the solvent is evaporated under low pressure. The residue is taken up with EtOAC and washed with a $Na_2CO_3$ saturated solution and a $NH_4Cl$ saturated solution. The organic phase is dried with anhydrous $Na_2SO_4$, filtered and concentrated under low pressure. The crude product is optionally purified by column chromatography on silica gel, to obtain the compounds of general structural formula VIII.

General Example of Procedure 2

The compound of structure VIII (1 equiv.) is dissolved in THF and MeOH (1:1) (8 mL/mmol), and the mixture is cooled to 0° C. with an ice bath. $NaBH_4$ (10 equiv.) is added slowly under magnetic stirring. The reaction mixture is left under stirring at 0° C. for 2 h. The disappearance of the starting compound is tested for by TLC (EtOAc/MeOH 85:15), and the solvent is evaporated under low pressure at the end of the reaction. The crude product is taken up with EtOAc and washed with a $NH_4Cl$ saturated solution. The organic phase dried with anhydrous $Na_2SO_4$ is filtered and concentrated under low pressure, and the resulting residue is purified by column chromatography on silica gel to obtain the compounds of general structure IX.

General Example of Procedure 3

Trifluoroacetic acid (10 equiv.) is slowly dripped into a solution of the N-protected aminoalcohol of structure IX in dichloromethane (10 mL/mmol), precooled to 0° C., under magnetic stirring. The reaction mixture is left under stirring at room temperature for 1.5 h. When the reaction is complete (TLC assay [EtOAc/MeOH 8:2]), the solvent is removed under low pressure. The residue is diluted in 2N HCl and loaded into a Dowex50WX2® ion-exchange resin column. The purification is carried out by washing with deionised water and eluting the aminoalcohol of structure X with a 10% aqueous solution of $NH_3$.

General Example of Procedure 4

A solution of intermediate VIII in DCM (10 mL/mmol) is cooled to 0° C. with an ice bath. TFA (10 equiv.) is dripped in, and the resulting mixture is left under stirring at room temperature for 2 h. On the disappearance of the starting product (TLC assay [EtOAc/MeOH 8:2]), the solvent and the excess TFA are removed under low pressure. The residue is dissolved in THF and the mixture is cooled to 0° C. An aqueous solution of 2N LiOH is slowly dripped in under magnetic stirring until a basic pH is reached, and the reaction mixture is left under stirring at room temperature until the reaction is complete (TLC assay [EtOAc/MeOH/ $NH_3$ 10% aqueous solution]). The reaction mixture is concentrated under low pressure, acidified with 2N HCl and loaded into a Dowex50WX2® ion-exchange resin column. After washing with deionised water, compound XI is released from the resin with a 10% aqueous solution of $NH_3$.

The following compounds were obtained with the general procedure described above.

Example 1: (S)-2-amino-N-(1-hydroxy-3-(1H-imidazol-4-yl)propan-2-yl)-2-methylpropanamide (code FLM-05 OLO)

(S)-methyl-2-(2-((tert-butoxycarbonyl)amino)-2-methylpropanamido)-3-(1H-imidazol-4-yl)propanoate (Procedure 1)
$^1$H NMR (300 MHz, CDCl3) δ 7.52 (s, 1H), 6.76 (s, 1H), 5.24 (br s, 1H), 4.70 (dd, J=11.2, 4.8 Hz, 1H), 3.70 (s, 3H), 3.33-3.18 (m, 1H), 3.11 (dd, J=15.0, 5.2 Hz, 1H), 1.49 (s, 6H), 1.42 (s, 9H).

(S)-tert-butyl(14(1-hydroxy-3-(1H-imidazol-4-yl)propan-2-yl)amino)-2-methyl-1-oxopropan-2-yl)carbamate (Procedure 2 Yield 46%).
$^1$H NMR (300 MHz, CD3OD) δ 7.61 (s, 1H), 6.87 (s, 1H), 4.20-4.00 (m, 1H), 3.58-3.45 (m, 2H), 2.88 (dd, J=14.9, 6.0 Hz, 1H), 2.77 (dd, J=14.9, 7.9 Hz, 1H), 1.42 (s, 9H), 1.36 (s, 3H), 1.32 (s, 3H).

(S)-2-amino-N-(1-hydroxy-3-(1H-imidazol-4-yl)propan-2-yl)-2-methylpropanamide (Procedure 3. Yield 79%.)
$^1$H NMR (300 MHz, CD3OD) δ 7.57 (s, 1H), 6.85 (s, 1H), 4.15-3.99 (m, 1H), 3.55 (d, J=5.1 Hz, 2H), 2.89 (dd, J=14.8, 6.0 Hz, 1H), 2.78 (dd, J=14.8, 8.0 Hz, 1H), 1.26 (s, 3H), 1.23 (s, 3H).

Example 2: (S)-3-amino-N-(1-hydroxy-3-(1H-imidazol-4-yl)propan-2-yl)-2,2-dimethylpropanamide (code FLM 04 OLO)

(S)-methyl-2-(3-((tert-butoxycarbonyl)amino)-2,2-dimethylpropanamido)-3-(1H-imidazol-4-yl)propanoate (procedure 1)
$^1$H NMR (300 MHz, CDCl$_3$) δ 7.59 (s, 1H), 7.54 (br s, 1H), 6.80 (s, 1H), 5.68 (br s, 1H), 4.74 (dd, J=11.9, 4.9 Hz, 1H), 3.70 (s, 3H), 3.35-3.03 (m, 4H), 1.42 (s, 9H), 1.22 (s, 3H), 1.20 (s, 3H).

(S)-tert-butyl(3-((1-hydroxy-3-(1H-imidazol-4-yl)propan-2-yl)amino)-2,2-dimethyl-3-oxopropyl) carbamate (Procedure 2, yield 80%).
$^1$H NMR (300 MHz, CD$_3$OD) δ 7.61 (s, 1H), 6.86 (s, 1H), 4.19-4.10 (m, 1H), 3.55 (d, J=5.5 Hz, 2H), 3.23-3.06 (m, 2H), 2.88 (dd, J=14.9, 5.9 Hz, 1H), 2.77 (dd, J=14.9, 8.2 Hz, 1H), 1.43 (s, 9H), 1.10 (s, 3H), 1.07 (s, 3H).

(S)-3-amino-N-(1-hydroxy-3-(1H-imidazol-4-yl)propan-2-yl)-2,2-dimethylpropanamide (Procedure 3, yield 92%).
$^1$H NMR (300 MHz, CD3OD) δ 7.56 (s, 1H), 6.84 (s, 1H), 4.22-4.12 (m, 1H), 3.55 (d, J=5.5 Hz, 2H), 2.88 (dd, J=14.8, 5.7 Hz, 1H), 2.77 (dd, J=14.8, 8.4 Hz, 1H), 2.65 (s, 2H), 1.11 (s, 3H), 1.09 (s, 3H).

Example 3: (S)-4-amino-N-(1-hydroxy-3-(1H-imidazol-4-yl)propan-2-yl)-2,2-dimethylbutanamide (code FLM 13 OLO)

(S)-methyl 2-(4-(tert-butoxycarbonylamino)-2,2-dimethylbutanamido)-3-(1H-imidazol-4-yl)propanoate (procedure 1)

$^1$H NMR (300 MHz, acetone) δ 7.99 (d, J=6.4 Hz, 1H), 7.70 (s, 1H), 6.98 (s, 1H), 6.05 (br s, 1H), 4.71-4.65 (m, 1H), 3.62 (s, 3H), 3.20-2.86 (m, 4H), 1.72 (dd, J=9.1, 5.6 Hz, 2H), 1.39 (s, 9H), 1.18 (s, 6H).

(S)-tert-butyl 4-(1-hydroxy-3-(1H-imidazol-4-yl)propan-2-ylamino)-3,3-dimethyl-4-oxobutylcarbamate (procedure 2, yield 68%)

$^1$H NMR (300 MHz, CD$_3$OD) δ 7.73 (s, 1H), 6.91 (s, 1H), 4.27-4.07 (m, 1H), 3.63-3.49 (m, 2H), 2.96-2.86 (m, 3H), 2.81 (dd, J=14.9, 8.6 Hz, 1H), 1.69-1.61 (m, 2H), 1.42 (s, 9H), 1.12 (s, 3H), 1.11 (s, 3H).

(S)-4-amino-N-(1-hydroxy-3-(1H-imidazol-4-yl)propan-2-yl)-2,2-dimethylbutanamide (67 mg, 0.27 mmol) (procedure 3, yield 83%.

$^1$H NMR (300 MHz, D$_2$O) δ 7.66 (s, 1H), 6.92 (s, 1H), 4.33-4.18 (m, 1H), 3.71-3.56 (m, 2H), 2.89 (dd, J=14.9, 4.7 Hz, 1H), 2.79-2.67 (m, 1H), 2.45-2.27 (m, 2H), 1.69-1.50 (m, 2H), 1.09 (s, 3H), 1.07 (s, 3H).

Example 4: (S)-1-(aminomethyl)-N-(1-hydroxy-3-(1H-imidazol-4-yl)propan-2-yl)cyclopropanecarboxamide (code FLM-9 OLO)

(S)-methyl 2-(1-(((tert-butoxycarbonyl)amino)methyl)cyclopropanecarboxamido)-3-(1H-imidazol-4-yl)propanoate (procedure 1)

$^1$H NMR (300 MHz, acetone-d$_6$) δ 8.08 (br s, 1H), 7.64 (s, 1H), 6.99 (s, 1H), 6.68 (br s, 1H), 4.59 (dd, J=12.7, 6.8 Hz, 1H), 3.61 (s, 3H), 3.44 (dd, J=15.0, 7.0 Hz, 1H), 3.29 (dd, J=15.0, 5.5 Hz, 1H), 3.07-2.95 (m, 2H), 1.43 (s, 9H), 1.10-0.99 (m, 2H), 0.85-0.75 (m, 2H).

(S)-tert-butyl ((1-((1-hydroxy-3-(1H-imidazol-4-yl)propan-2-yl)carbamoyl)cyclopropyl)methyl) carbamate (procedure 2, yield 93%).

$^1$H NMR (300 MHz, CD$_3$OD) δ 7.61 (s, 1H), 6.87 (s, 1H), 4.17-4.08 (m, 1H), 3.53 (d, J=5.4 Hz, 2H), 3.27 (s, 2H), 2.90 (dd, J=14.8, 6.0 Hz, 1H), 2.75 (dd, J=14.8, 8.1 Hz, 1H), 1.44 (s, 9H), 1.09-1.01 (m, 2H), 0.75-0.72 (m, 2H).

(S)-1-(aminomethyl)-N-(1-hydroxy-3-(1H-imidazol-4-yl)propan-2-yl)cyclopropanecarboxamide (procedure 3, yield 86%).

$^1$H NMR (300 MHz, CD$_3$OD) δ 7.57 (s, 1H), 6.84 (s, 1H), 4.19-4.08 (m, 1H), 3.55 (d, J=5.3 Hz, 2H), 2.92-2.71 (m, 4H), 1.09-0.97 (m, 2H), 0.74-0.63 (m, 2H).

Example 5: (S)-1-(aminomethyl)-N-(1-hydroxy-3-(1H-imidazol-4-yl)propan-2-yl)cyclobutanecarboxamide (code FLM-10 OLO)

(S)-methyl 2-(1-(((tert-butoxycarbonyl)amino)methyl)cyclobutanecarboxamido)-3-(1H-imidazol-4-yl)propanoate (procedure 1)

$^1$H NMR (300 MHz, CD$_3$OD) δ 7.61 (s, 1H), 6.89 (s, 1H), 4.67 (dd, J=8.3, 5.3 Hz, 1H), 3.71 (s, 3H), 3.48-3.33 (m, 2H), 3.16 (dd, J=14.8, 5.2 Hz, 1H), 3.06 (dd, J=14.8, 8.4 Hz, 1H), 2.32-2.13 (m, 2H), 2.04-1.85 (m, 3H), 1.84-1.67 (m, 1H), 1.43 (s, 9H).

(S)-tert-butyl ((1-((1-hydroxy-3-(1H-imidazol-4-yl)propan-2-yl) carbamoyl)cyclobutyl)methyl) carbamate (procedure 2, yield 73%).

$^1$H NMR (300 MHz, CD$_3$OD) δ 7.60 (s, 1H), 6.87 (s, 1H), 4.20-4.12 (m, 1H), 3.61-3.51 (m, 2H), 3.45-3.31 (m, 2H), 2.87 (dd, J=14.8, 6.0 Hz, 1H), 2.78 (dd, J=14.8, 8.2 Hz, 1H), 2.31-2.09 (m, 2H), 2.01-1.80 (m, 3H), 1.80-1.60 (m, 1H), 1.41 (s, 9H).

(S)-1-(aminomethyl)-N-(1-hydroxy-3-(1H-imidazol-4-yl)propan-2-yl)cyclobutanecarboxamide (procedure 3, yield 96%).

$^1$H NMR (300 MHz, CD$_3$OD) δ 7.57 (s, 1H), 6.86 (s, 1H), 4.26-4.13 (m, 1H), 3.66-3.48 (m, 2H), 2.97-2.83 (m, 3H), 2.76 (dd, J=14.8, 8.7 Hz, 1H), 2.37-2.17 (m, 2H), 2.00-1.67 (m, 4H).

Example 6: (S)-1-(aminomethyl)-N-(1-hydroxy-3-(1H-imidazol-4-yl)propan-2-yl)cyclopentanecarboxamide (code FLM-11 OLO)

(S)-methyl 2-(1-(((tert-butoxycarbonyl)amino)methyl)cyclopentanecarboxamido)-3-(1H-imidazol-4-yl)propanoate (procedure 1)

$^1$H NMR (300 MHz, CD$_3$OD) δ 7.59 (s, 1H), 6.87 (s, 1H), 4.64 (dd, J=8.3, 5.3 Hz, 1H), 3.71 (s, 3H), 3.24 (d, J=6.1 Hz, 2H), 3.15 (dd, J=14.7, 5.1 Hz, 1H), 3.06 (dd, J=14.8, 8.4 Hz, 1H), 1.97-1.78 (m, 2H), 1.73-1.51 (m, 6H), 1.43 (s, 9H).

(S)-tert-butyl ((1-((1-hydroxy-3-(1H-imidazol-4-yl)propan-2-yl)carbamoyl)cyclopentyl)methyl) carbamate (procedure 2, yield 92%).

$^1$H NMR (300 MHz, acetone-d$_6$) δ 7.69 (s, 1H), 7.17 (d, J=7.4 Hz, 1H), 6.94 (s, 1H), 6.44 (br s, 1H), 6.06 (br s, 2H), 4.16-4.03 (m, 1H), 3.58-3.41 (m, 2H), 3.31 (dd, J=13.8, 6.7 Hz, 1H), 3.22 (dd, J=13.7, 6.1 Hz, 1H), 2.93-2.78 (m, 2H), 2.02-1.82 (m, 2H), 1.71-1.50 (m, 6H), 1.40 (s, 9H).

(S)-1-(aminomethyl)-N-(1-hydroxy-3-(1H-imidazol-4-yl)propan-2-yl)cyclopentanecarboxamide (procedure 3, yield 78%).

$^1$H NMR (300 MHz, CD$_3$OD) δ 7.56 (s, 1H), 6.84 (s, 1H), 4.25-4.14 (m, 1H), 3.62-3.49 (m, 2H), 2.88 (dd, J=14.8, 5.6 Hz, 1H), 2.77 (dd, J=14.9, 8.7 Hz, 1H), 2.71 (s, 2H), 2.03-1.86 (m, 2H), 1.68-1.44 (m, 6H).

Example 7: (S)-1-(aminomethyl)-N-(1-hydroxy-3-(1H-imidazol-4-yl)propan-2-yl)cyclohexanecarboxamide (code FLM-14 OLO)

(S)-methyl 2-(1-(((tert-butoxycarbonylamino)methyl)cyclohexanecarboxamido)-3-(1H-imidazol-4-yl)propanoate (procedure 3)

$^1$H NMR (300 MHz, CD$_3$OD) δ 7.62 (s, 1H), 6.89 (s, 1H), 4.69 (dd, J=8.5, 5.2 Hz, 1H), 3.73 (s, 3H), 3.23-3.04 (m, 4H), 2.03-1.89 (m, 2H), 1.61-1.48 (m, 3H), 1.43 (s, 9H), 1.37-1.16 (m, 5H).

(S)-tert-butyl (1-(1-hydroxy-3-(1H-imidazol-4-yl)propan-2-ylcarbamoyl)-cyclohexyl)methyl carbamate (procedure 2, yield 88%).

$^1$H NMR (300 MHz, CD$_3$OD) δ 7.59 (s, 1H), 6.87 (s, 1H), 4.28-4.15 (m, 1H), 3.63-3.50 (m, 2H), 3.23-3.12 (m, 1H), 3.10-2.99 (m, 1H), 2.93-2.74 (m, 2H), 2.03-1.86 (m, 2H), 1.59-1.46 (m, 3H), 1.42 (s, 9H), 1.36-1.08 (m, 5H).

(S)-1-(aminomethyl)-N-(1-hydroxy-3-(1H-imidazol-4-yl)propan-2-yl)cyclohexanecarboxamide (procedure 3, yield 92%).

$^1$H NMR (300 MHz, CD$_3$OD) δ 7.56 (s, 1H), 6.86 (s, 1H), 4.36-4.19 (m, 1H), 3.65-3.50 (m, 2H), 2.88 (dd, J=14.9, 5.4 Hz, 1H), 2.78 (dd, J=14.9, 9.0 Hz, 1H), 2.58 (s, 2H), 2.06-1.94 (m, 2H), 1.60-1.44 (m, 3H), 1.36-1.11 (m, 5H).

Example 8: (S)-3-amino-N-(1-hydroxy-3-(1-methyl-1H-imidazol-5-yl)propan-2-yl)-2,2-dimethylpropanamide (FLM-12 OLO)

(S)-methyl 2-(3-((tert-butoxycarbonyl)amino)-2,2-dimethylpropanamido)-3-(1-methyl-1H-imidazol-5-yl)propanoate (procedure 1)

¹H NMR (300 MHz, CD₃OD) δ 7.54 (s, 1H), 6.75 (s, 1H), 4.68 (dd, J=9.7, 5.4 Hz, 1H), 3.74 (s, 3H), 3.66 (s, 3H), 3.23 (dd, J=15.5, 5.4 Hz, 1H), 3.15 (s, 2H), 3.08 (dd, J=15.5, 9.8 Hz, 1H), 1.43 (s, 9H), 1.11 (s, 3H), 1.08 (s, 3H).

(S)-tert-butyl (3-((1-hydroxy-3-(1-methyl-1H-imidazol-5-yl)propan-2-yl)amino)-2,2-dimethyl-3-oxopropyl)carbamate (procedure 2, yield 91%).

¹H NMR (300 MHz, CD₃OD) δ 7.55 (s, 1H), 6.75 (s, 1H), 4.22-4.10 (m, 1H), 3.69 (s, 3H), 3.58 (d, J=5.4 Hz, 2H), 3.21-3.05 (m, 2H), 2.91 (dd, J=15.4, 5.7 Hz, 1H), 2.75 (dd, J=15.3, 9.2 Hz, 1H), 1.43 (s, 9H), 1.09 (s, 3H), 1.05 (s, 3H).

(S)-3-amino-N-(1-hydroxy-3-(1-methyl-1H-imidazol-5-yl)propan-2-yl)-2,2-dimethylpropanamide (procedure 3, yield 73%).

¹H NMR (300 MHz, CD₃OD) δ 7.51 (s, 1H), 6.74 (s, 1H), 4.25-4.15 (m, 1H), 3.68 (s, 3H), 3.59 (d, J=5.4 Hz, 2H), 2.90 (dd, J=15.3, 5.6 Hz, 1H), 2.76 (dd, J=15.3, 9.4 Hz, 1H), 2.64 (s, 2H), 1.11 (s, 3H), 1.07 (s, 3H).

Example 9: (S)-3-amino-N-(1-hydroxy-3-(1H-imidazol-4-yl)propan-2-yl)-3,3-dimethylpropanamide (FLM-02 OLO)

(S)-methyl-2-(3-((tert-butoxycarbonyl)amino)-3,3-dimethylpropanamido)-3-(1H-imidazol-4-yl)propanoate (procedure 1)

¹H NMR (300 MHz, CDCl₃) δ 7.60 (s, 1H), 7.15 (d, J=7.3 Hz, 1H), 6.83 (s, 1H), 5.39 (s, 1H), 4.88-4.74 (m, 1H), 3.70 (s, 3H), 3.12 (d, J=5.3 Hz, 2H), 2.56 (q, J=13.7 Hz, 2H), 1.41 (s, 9H), 1.38 (s, 3H), 1.37 (s, 3H).

(S)-tert-butyl(3-((1-hydroxy-3-(1H-imidazol-4-yl)propan-2-yl)amino)-3,3-dimethyl-3-oxopropyl) carbamate (procedure 2, yield 81%).

¹H NMR (300 MHz, CD₃OD) δ 7.64 (s, 1H), 6.89 (s, 1H), 4.20-4.05 (m, 1H), 3.53 (d, J=5.2 Hz, 2H), 2.89 (dd, J=14.9, 6.0 Hz, 1H), 2.74 (dd, J=14.9, 8.2 Hz, 1H), 2.45 (s, 2H), 1.42 (s, 9H), 1.29 (s, 3H), 1.26 (s, 3H).

(S)-3-amino-N-(1-hydroxy-3-(1H-imidazol-4-yl)propan-2-yl)-3,3-dimethylpropanamide (procedure 3, yield 90%).

¹H NMR (300 MHz, CD₃OD) δ 7.56 (s, 1H), 6.85 (s, 1H), 4.22-4.10 (m, 1H), 3.61-3.48 (m, 2H), 2.88 (dd, J=14.9, 5.7 Hz, 1H), 2.73 (dd, J=14.9, 8.5 Hz, 1H), 2.22 (s, 2H), 1.11 (s, 3H), 1.09 (s, 3H).

Example 10: (S)-3-amino-2,2-difluoro-N-(1-hydroxy-3-(1H-imidazol-4-yl)propan-2-yl)propanamide (FLM-07-OLO)

The compound was prepared with a slightly different procedure by coupling between (S)-2-amino-3-(1H-imidazol-4-yl)propyl acetate and Fmoc-3-amino-2,2-difluoropropionyl chloride.

The resulting compound (S)-2-(3-(((9H-fluoren-9-yl)methoxy)carbonylamino)-2,2-difluoropropanamido)-3-(1H-imidazol-4-yl)propyl acetate was then deprotected to give the final aminoalcohol.

(S)-2-(3-(((9H-fluoren-9-yl)methoxy)carbonylamino)-2,2-difluoropropanamido)-3-(1H-imidazol-4-yl)propyl acetate (Yield 70%).

¹H NMR (300 MHz, CD₃OD) δ 7.79 (d, J=7.5 Hz, 2H), 7.64 (d, J=7.5 Hz, 2H), 7.58 (s, 1H), 7.38 (t, J=7.3 Hz, 2H), 7.30 (t, J=7.3 Hz, 2H), 6.87 (s, 1H), 4.44-4.32 (m, 3H), 4.25-4.15 (m, 2H), 4.07-3.99 (m, 1H), 3.70 (t, J=14.5 Hz, 2H), 2.93-2.77 (m, 2H), 2.01 (s, 3H).

(S)-3-amino-2,2-difluoro-N-(1-hydroxy-3-(1H-imidazol-4-yl)propan-2-yl)propanamide (Yield 99%)

¹H NMR (300 MHz, D₂O) δ 7.73 (s, 1H), 6.97 (s, 1H), 4.38-4.22 (m, 1H), 3.79 (dd, J=11.7, 4.6 Hz, 1H), 3.66 (dd, J=11.8, 7.4 Hz, 1H), 3.05 (t, J=15.3 Hz, 2H), 2.95 (dd, J=14.9, 4.9 Hz, 1H), 2.77 (dd, J=14.9, 10.0 Hz, 1H).

Example 11: N-(2-amino-2-methylpropanoyl)-L-histidine (FLM-05-ACI)

(procedure 4. Yield 80%)

¹H NMR (300 MHz, D₂O) δ 7.75 (s, 1H), 6.93 (s, 1H), 4.45 (dd, J=9.0, 4.9 Hz, 1H), 3.16 (dd, J=15.0, 4.8 Hz, 1H), 2.98 (dd, J=15.0, 9.0 Hz, 1H), 1.49 (s, 3H), 1.37 (s, 3H).

Example 12: N-(3-amino-2,2-dimethylpropanoyl)-L-histidine (FLM-04-ACI)

(procedure 4. Yield 65%)

¹H NMR (300 MHz, D₂O) δ 7.73 (s, 1H), 6.95 (s, 1H), 4.46 (dd, J=8.7, 4.8 Hz, 1H), 3.18 (dd, J=15.0, 4.9 Hz, 1H), 3.11-2.95 (m, 3H), 1.29 (s, 3H), 1.16 (s, 3H).

Example 13: N-(1-aminomethyl)-1-cyclopropylcarbonyl)-L-histidine. (FLM-09-ACI)

(procedure 4. Yield 99%)

¹H NMR (300 MHz, D₂O) δ 7.64 (s, 1H), 6.89 (s, 1H), 4.42 (dd, J=8.7, 4.8 Hz, 1H), 3.16-2.82 (m, 4H), 1.22-1.07 (m, 1H), 1.05-0.83 (m, 3H).

Example 14: N-(1-aminomethyl)-1-cyclobutylcarbonyl)-L-histidine (FLM-10-ACI)

(procedure 4. Yield 93%)

¹H NMR (300 MHz, D₂O) δ 7.77 (s, 1H), 7.01 (s, 1H), 4.52 (dd, J=9.1, 4.7 Hz, 1H), 3.42-3.29 (m, 2H), 3.24 (dd, J=15.0, 4.6 Hz, 1H), 3.04 (dd, J=15.0, 9.1 Hz, 1H), 2.43-2.19 (m, 2H), 2.18-1.93 (m, 3H), 1.92-1.78 (m, 1H).

Example 15: N-(1-aminomethyl)-1-cyclopentylcarbonyl)-L-histidine (FLM-11-ACI)

(procedure 4. Yield 99%)

¹H NMR (300 MHz, CD₃OD) δ 7.56 (s, 1H), 6.83 (s, 1H), 4.45 (dd, J=8.1, 4.3 Hz, 1H), 3.23 (dd, J=14.9, 4.3 Hz, 1H), 3.10-2.93 (m, 3H), 2.18-1.95 (m, 2H), 1.75-1.47 (m, 6H).

Example 16: N-(1-aminomethyl)-1-cyclohexylcarbonyl)-L-histidine (FLM-14-ACI)

(procedure 4. Yield 100%)

¹H NMR (300 MHz, CD₃OD) δ 7.56 (s, 1H), 6.84 (s, 1H), 4.48 (dd, J=8.6, 4.3 Hz, 1H), 3.26 (dd, J=15.0, 4.5 Hz, 1H), 3.05 (dd, J=15.0, 8.7 Hz, 1H), 2.98-2.79 (m, 2H), 2.10 (d, J=12.2 Hz, 2H), 1.64-1.45 (m, 3H), 1.45-1.12 (m, 5H).

Example 17: N-(4-amino-2,2-dimethylbutanoyl)-L-histidine (FLM-13-ACI)

(procedure 4. Yield 100%)
$^1$H NMR (300 MHz, D$_2$O) δ 7.59 (s, 1H), 6.86 (s, 1H), 4.40 (dd, J=9.1, 4.7 Hz, 1H), 3.08 (dd, J=14.9, 4.7 Hz, 1H), 2.90 (dd, J=14.9, 9.1 Hz, 1H), 2.58-2.38 (m, 2H), 1.67-1.56 (m, 2H), 1.07 (s, 3H), 1.04 (s, 3H).

Example 18: N-(3-amino-3,3-dimethylpropanoyl)-L-histidine (FLM-02-ACI)

(procedure 4. Yield 100%)
$^1$H NMR (300 MHz, D$_2$O) δ 7.65 (s, 1H), 6.93 (s, 1H), 4.49 (dd, J=9.8, 4.4 Hz, 1H), 3.15 (dd, J=15.0, 4.4 Hz, 1H), 2.92 (dd, J=14.9, 9.9 Hz, 1H), 2.37 (s, J=14.1 Hz, 2H), 1.13 (s, 3H), 1.08 (s, 3H).

Example 19: N-(3-amino-2,2-dimethylpropanoyl)-L-histidine (FLM-12-ACI)

(procedure 4. Yield 90%)
$^1$H NMR (300 MHz, D$_2$O) δ 7.69 (s, 1H), 6.86 (s, 1H), 4.53 (dd, J=10.0, 4.8 Hz, 1H), 3.70 (s, 3H), 3.26 (dd, J=15.5, 4.7 Hz, 1H), 3.13-2.96 (m, 3H), 1.32 (s, 3H), 1.17 (s, 3H).

Example 20: N-(3-amino-2,2-difluoropropanoyl)-L-histidine (FLM-07-ACI)

(procedure 4. Yield 95%)
$^1$H NMR (300 MHz, D$_2$O) δ 8.16 (s, 1H), 7.11 (s, 1H), 4.53 (dd, J=9.1, 4.8 Hz, 1H), 3.34-3.23 (m, 3H), 3.07 (dd, J=15.2, 9.2 Hz, 1H).
$^1$H NMR (300 MHz, D$_2$O) δ 8.16 (s, 1H), 7.11 (s, 1H), 4.53 (dd, J=9.1, 4.8 Hz, 1H), 3.34-3.23 (m, 3H), 3.07 (dd, J=15.2, 9.2 Hz, 1H).

Pharmacological Tests

The carbonyl-quenching activity of a selected series of compounds according to the invention has been demonstrated in vitro by incubating HNE (50 μM) with the molecule under study (1 mM), in phosphate buffer (10 mM), pH 7.4, at 37° C. The activity was evaluated one and three hours after incubation, determining the residual HNE content by reverse-phase chromatography as previously described by Aldini G. et al. [Biochem Biophys Res Commun. 2002 Nov. 15; 298 (5):699-706]. The carbonyl-quenching activity is evaluated on the basis of the percentage of HNE reacted, compared with the HNE content in the absence of the molecule to be tested.

The stability in human serum of the compound most active in the preceding test was also evaluated by incubation at 37° C. and subsequent sampling at 0 min, 15 min, 30 min, 1 h and 2 h. The samples taken from each matrix, suitably treated, were analysed by HPLC-MS, obtaining recovery after 1 h and 2 h.

The results are summarised in the tables below:

TABLE I

| COMPOUND | ACTIVITY (CARNOSINE UNIT) | | HNE CONSUMPTION (%) | |
|---|---|---|---|---|
| | 1 h | 3 h | 1 h | 3 h |
| FLM-02-ACI | 0.02 | 0.14 | 0.40 ± 1.73 | 6.05 ± 1.66 |
| FLM-04-ACI | 1.76 | 1.51 | 30.06 ± 4.68 | 64.44 ± 4.37 |
| FLM-05-ACI | 0.33 | 0.37 | 5.58 ± 7.50 | 15.84 ± 10.65 |
| FLM-07-ACI | 0.46 | 0.69 | 7.88 ± 5.41 | 29.42 ± 6.42 |
| FLM-09-ACI | 0.81 | 0.89 | 13.70 ± 0.83 | 36.11 ± 2.87 |
| FLM-10-ACI | 1.06 | 1.11 | 17.89 ± 1.97 | 45.04 ± 2.94 |
| FLM-11-ACI | 1.41 | 1.31 | 23.82 ± 1.55 | 53.54 ± 1.10 |
| FLM-12-ACI | 1.58 | 1.20 | 27.07 ± 9.77 | 51.35 ± 9.22 |
| FLM-13-ACI | 0.69 | 0.48 | 11.77 ± 6.79 | 20.43 ± 7.94 |
| FLM-14-ACI | 1.71 | 1.36 | 29.10 ± 2.97 | 58.03 ± 2.37 |
| FLM-02-OLO | 0.25 | 0.24 | 4.09 ± 2.61 | 10.50 ± 2.24 |
| FLM-04-OLO | 3.13 | 2.00 | 52.14 ± 5.56 | 86.47 ± 2.73 |
| FLM-05-OLO | 0.38 | 0.45 | 6.40 ± 1.72 | 19.44 ± 2.36 |
| FLM-07-OLO | 1 | 0.82 | 17.07 ± 1.76 | 34.93 ± 0.58 |
| FLM-09-OLO | 1.55 | 1.45 | 26.21 ± 1.04 | 59.09 ± 1.49 |
| FLM-10-OLO | 2.82 | 2.08 | 47.68 ± 3.02 | 84.63 ± 2.70 |
| FLM-11-OLO | 2.82 | 2.06 | 47.56 ± 0.69 | 83.90 ± 0.33 |
| FLM-12-OLO | 2.98 | 1.64 | 50.77 ± 3.84 | 70.08 ± 2.98 |
| FLM-13-OLO | 0.62 | 0.54 | 10.54 ± 10.04 | 23.05 ± 12.28 |
| FLM-14-OLO | 2.84 | 1.96 | 48.36 ± 6.22 | 83.50 ± 5.85 |
| BLANK | 0.12 | 0.04 | 2.00 ± 0.66 | 1.88 ± 0.69 |
| CARNOSINE | 1.00 | 1.00 | 17.05 ± 1.24 | 42.66 ± 0.89 |

TABLE II

| COMPOUND | Stability in plasma (% residual amount) | |
|---|---|---|
| | 1 h | 2 h |
| FLM-04-OL | 101.78 ± 16.20 | 100.34 ± 9.46 |

The invention claimed is:
1. A compound of general formula I

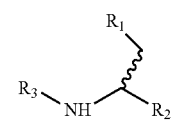

wherein:
R1 is imidazole optionally substituted at the nitrogen atom at the 1-position or at the 3-position with methyl, ethyl or propyl;
R2 is a CH$_2$O—R group wherein R is hydrogen, a straight or branched C$_1$-C$_{10}$ alkyl group or a C$_3$-C$_8$ cycloalkyl group, a straight or branched C$_1$-C$_8$ alkylcarbonyl group, a C$_3$-C$_8$ cycloalkylcarbonyl group; or R is an Ar(CH$_2$)$_p$C(=O)— group wherein Ar is aryl selected from phenyl and naphthyl optionally substituted with one or two groups selected from the group consisting of methyl, methoxy or ethyl and p is zero or an integer ranging from 1 to 3;
R$_3$ is a group of general formula II

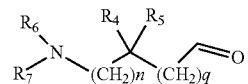

wherein
n and q, independently one from the other, are zero or are an integer ranging from 1 to 4;

$R_6$ and $R_7$, which can be the same or different, are:
  hydrogen;
  a straight or branched $C_1$-$C_{20}$ alkylcarbonyl or $C_3$-$C_7$ cycloalkylcarbonyl group optionally containing one or more double bonds, or an $Ar(CH_2)_pC(=O)-$ group wherein Ar and p are as defined above;
  a straight or branched $C_1$-$C_{10}$ alkoxycarbonyl or $C_3$-$C_7$ cycloalkoxycarbonyl group optionally containing one or more double bonds or an $ArO(CH_2)_nC(=O)-$ group wherein Ar and p are as defined above;
  one of $R_6$ and $R_7$ is an amino group and the other is hydrogen;
  one or $R_6$ and $R_7$ is hydrogen and the other is a group of formula III

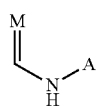

wherein M is nitrogen, oxygen or sulphur and A is hydrogen or an amino group, and the free valence of the carbon atom forms a bond with the nitrogen atom of the group of formula II;
$R_4$ and $R_5$, which can be the same or different, are:
  a straight or branched $C_1$-$C_8$ alkyl group;
  a halogen;
  can be linked to form, together with the carbon atom to which they are bonded, a C3-C6 cycloaliphatic ring selected from cyclopropyl, cyclobutyl, cyclopentyl and cyclohexyl, forming an $R_3$ group of general formula IV

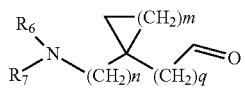

wherein
m has a value ranging from 1 to 4;
$R_6$, $R_7$, n and q have the meanings described above;
wherein:
in general formula I, wavy bond ⁓⁓⁓ indicates that the carbon atom substituted with NH and $R_2$ can have the R or S configuration;
in general formulas II and IV the free valence of the carbon atom of the carbonyl group forms a bond with the nitrogen atom of formula I;
the optical isomers and diastereomers thereof, either in isolated or mixture form, and the pharmacologically acceptable salts thereof.

2. The compound according to claim 1 wherein:
$R_2$ is $CH_2-OH$;
$R_3$ is a group of formula II wherein $R_4$ and $R_5$ are both methyl or halogen, $R_6$ and $R_7$ are both hydrogen or one of $R_6$ and $R_7$ is hydrogen and the other is a straight or branched $C_1$-$C_{10}$ alkoxycarbonyl or a $C_3$-$C_7$ cyclic group, and n and q are as defined above.

3. The compound according to claim 1 wherein:
$R_2$ is $CH_2-OH$;
$R_3$ is a group of formula IV wherein $R_4$ and $R_5$ are joined to form, together with the carbon atom to which they are bonded, a $C_3$-$C_6$ cycloaliphatic ring selected from cyclopropyl, cyclobutyl, cyclopentyl and cyclohexyl; $R_6$ and $R_7$ are both hydrogen or one of $R_6$ and $R_7$ is hydrogen and the other is a straight or branched $C_1$-$C_{10}$ alkoxycarbonyl or a $C_3$-$C_7$ cyclic group, and m, n and q are as defined above.

4. The compound according to claim 1 wherein:
$R_2$ is $CH_2-OH$;
$R_3$ is a group of formula II wherein $R_4$ and $R_5$ are both methyl or fluorine, $R_6$ and $R_7$ are both hydrogen, and n and q are as defined above.

5. The compound according to claim 1 wherein:
$R_2$ is $CH_2-OH$;
$R_3$ is a group of formula IV wherein $R_4$ and $R_5$ are joined to form, together with the carbon atom to which they are bonded, a C3-C6 cycloaliphatic ring selected from cyclopropyl, cyclobutyl, cyclopentyl and cyclohexyl; $R_6$ and $R_7$ are both hydrogen, and m, n and q are as defined above.

6. The compound according to claim 1 selected from:
(S)-2-amino-N-(1-hydroxy-3-(1H-imidazol-4-yl)propan-2-yl)-2-methylpropanamide;
(S)-3-amino-N-(1-hydroxy-3-(1H-imidazol-4-yl)propan-2-yl)-2,2-dimethylpropanamide;
(S)-4-amino-N-(1-hydroxy-3-(1H-imidazol-4-yl)propan-2-yl)-2,2-dimethylbutanamide;
(S)-1-(aminomethyl)-N-(1-hydroxy-3-(1H-imidazol-4-yl)propan-2-yl)cyclopropanecarboxamide;
(S)-1-(aminomethyl)-N-(1-hydroxy-3-(1H-imidazol-4-yl)propan-2-yl)cyclobutanecarboxamide;
(S)-1-(aminomethyl)-N-(1-hydroxy-3-(1H-imidazol-4-yl)propan-2-yl)cyclopentanecarboxamide;
(S)-1-(aminomethyl)-N-(1-hydroxy-3-(1H-imidazol-4-yl)propan-2-yl)cyclohexanecarboxamide;
(S)-3-amino-N-(1-hydroxy-3-(1-methyl-1H-imidazol-5-yl)propan-2-yl)-2,2-dimethylpropanamide;
(S)-3-amino-N-(1-hydroxy-3-(1H-imidazol-4-yl)propan-2-yl)-3,3-dimethylpropanamide;
(S)-3-amino-2,2-difluoro-N-(1-hydroxy-3-(1H-imidazol-4-yl)propan-2-yl)propanamide.

7. A pharmaceutical composition comprising one or more of the compounds according to claim 1 in combination with suitable excipients.

8. The compound according to claim 2 wherein:
$R_3$ is a group of formula II wherein $R_4$ and $R_5$ are both methyl or fluorine, $R_6$ and $R_7$ are both hydrogen, and n and q are as defined above.

9. The compound according to claim 3 wherein:
$R_3$ is a group of formula IV wherein $R_4$ and $R_5$ are joined to form, together with the carbon atom to which they are bonded, a C3-C6 cycloaliphatic ring selected from cyclopropyl, cyclobutyl, cyclopentyl and cyclohexyl, $R_6$ and $R_7$ are both hydrogen, and m, n and q are as defined above.

\* \* \* \* \*